US00PP36402P2

(12) United States Plant Patent
Bell

(10) Patent No.: US PP36,402 P2
(45) Date of Patent: Jan. 21, 2025

(54) BLUEBERRY PLANT NAMED 'Ridley7301'

(50) Latin Name: ***Vaccinium* hybrid**
Varietal Denomination: Ridley7301

(71) Applicant: MOUNTAIN BLUE ORCHARDS PTY LTD, Lindendale (AU)

(72) Inventor: Ridley Bell, Lindendale (AU)

(73) Assignee: Mountain Blue Orchards PTY LTD, Lindendale (AU)

( * ) Notice: Subject to any disclaimer, the term of this patent is extended or adjusted under 35 U.S.C. 154(b) by 0 days.

(21) Appl. No.: 18/445,950

(22) Filed: Apr. 11, 2024

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC . A01H 5/08; A01H 5/00; A01H 6/368; A01H 6/36
See application file for complete search history.

(56) References Cited

U.S. PATENT DOCUMENTS

PP20,695 P2 2/2010 Wright et al.
PP26,972 P3 * 7/2016 Bell ..... A01H 6/368 Plt./157
PP31,605 P3 3/2020 Bell

OTHER PUBLICATIONS

Upov Pluto 20240729 for Ridley 4507retrieved on Jul. 29, 2024 at https://pluto.upov.int/result, 3 pp. (Year: 2024).*

* cited by examiner

*Primary Examiner* — June Hwu
(74) *Attorney, Agent, or Firm* — Hunt IP Law

(57) ABSTRACT

The new blueberry plant variety 'Ridley7301' is a new and distinct low-chill tetraploid highbush blueberry (*Vaccinium*) variety of complex hybrid ancestry, based largely on *V. corymbosum* with some genes of *V. darrowi*. 'Ridley7301' is a commercial variety intended for use as fresh fruit for shipping, hand pick, customer pick, machine harvest and processing markets and as a home garden plant. The variety is produced from a cross of seed parent 'M07-05-03' (unpatented) and with pollen parent 'Ridley 4507' (US unpatented, AU PBR Cert. 6076), and can be distinguished by its outstanding features.

5 Drawing Sheets

Latin name of the genus and species:
Genus—*Vaccinium.*
Species—hybrid.
Variety denomination: The new blueberry plant claimed is of the variety denominated 'Ridley7301'.

BACKGROUND OF THE INVENTION

The present invention relates to a new and distinct perennial variety of *Vaccinium* variety of complex hybrid ancestry, based largely on *V. corymbosum* with some genes of *V. darrowi* (Southern Highbush Blueberry), which has been given the variety denomination of 'Ridley7301'. Its market class is that of a fruiting plant. 'Ridley7301' is intended for use as fresh fruit for shipping, customer pick and processing markets and as a home garden plant.

The new *Vaccinium* hybrid cultivar is a selection resulting from seedlings produced in a breeding program of *Vaccinium* at Lindendale, New Sout Wales, Australia in 2015 from the controlled pollination of seed parent 'M07-05-03' (unpatented) with pollen parent 'Ridley 4507' (US unpatented. AU PBR Cert. 6076). The seed parent was produced from a seedling selection of seed parent 'S01-28-05' (unpatented) and pollen parent 'S01-29-01' (unpatented). The pollen parent was produced from a seedling selection of seed parent 'C99-42' (U.S. Plant Pat. No. 20,695) and pollen parent 'C00-008' (unpatented).

The new cultivar was discovered and selected as a single plant within a population of 100 resulting *Vaccinium* plants from this controlled pollination in 2018 in a commercial field plantation environment at Tabulam, New South Wales, Australia.

The new blueberry cultivar was designated 'M18-73-01' and has been planted in replicated trials since 2019 at the commercial farms at Tabulam, New South Wales, Australia.

Asexual reproduction of the new cultivar by cutting propagation since 2018 at Lindendale, New South Wales, Australia has demonstrated that the new cultivar reproduces true to type with all of the characteristics, as herein described, firmly fixed and retained through successive generations of such asexual propagation.

SUMMARY OF THE INVENTION

The following are the most outstanding and distinguishing characteristics of the new cultivar when grown under normal horticultural practices in Tabulam, New South Wales, Australia and that have been repeatedly observed and can be used to distinguish 'M18-73-01' ('Ridley7301') as a new and distinct cultivar of *Vaccinium* plant:

1. very large fruit size;
2. firm and juicy fruit crunch;
3. firm and juicy fruit texture;
4. excellent waxy bloom coating on fruit;
5. sweet flavor;

6. vigorous growth;
7. semi-upright bush shape;
8. early-season timing of flowering and fruiting; and
9. suitability to machine harvesting.

BRIEF DESCRIPTION OF THE DRAWINGS

The accompanying photographic illustrations show the typical appearance of the new variety 'Ridley7301'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
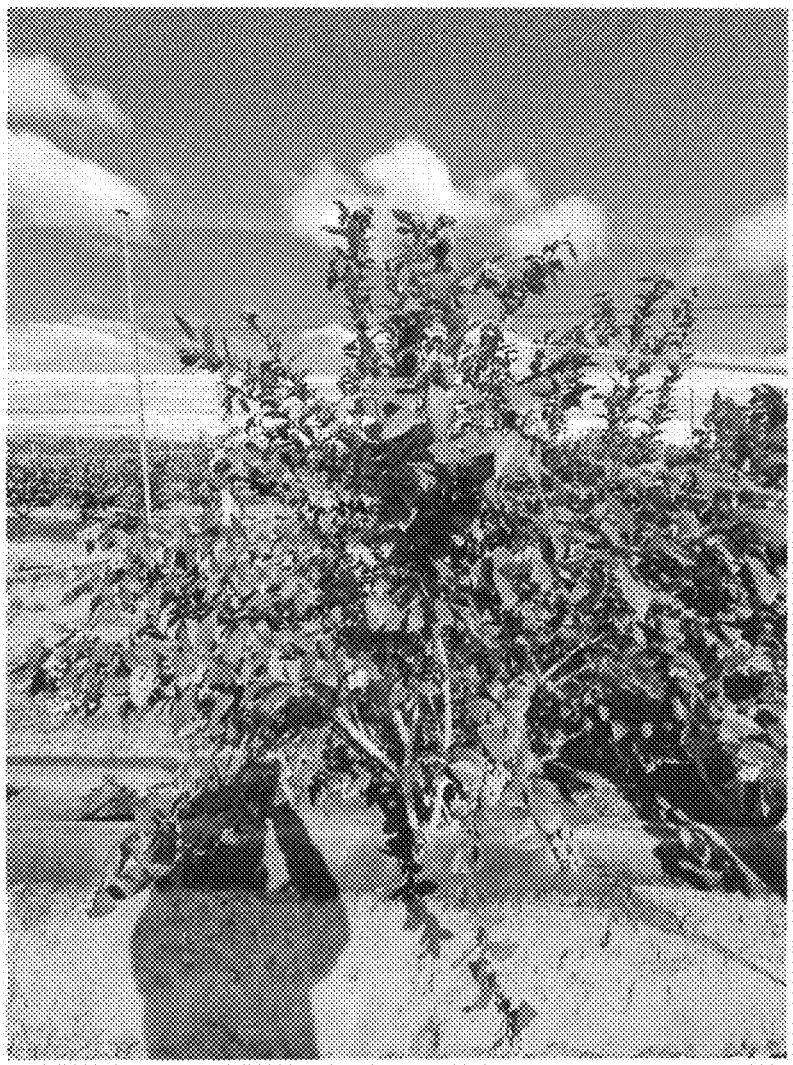
FIG. 1 is a photograph of the new variety 'Ridley7301', demonstrating the plant's semi-upright growth habit.
Figure 2:
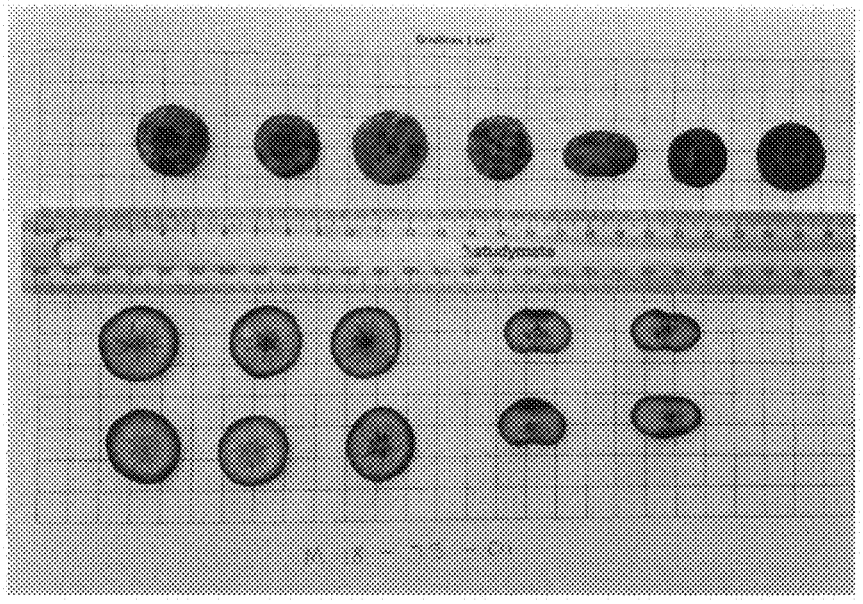
FIG. 2 is a photograph of the fruit of the new variety 'Ridley7301'. Top row depicts top, bottom, and side views of the fruit. Middle and bottom rows depict cross section and longitudinal views of the fruit.
Figure 3:
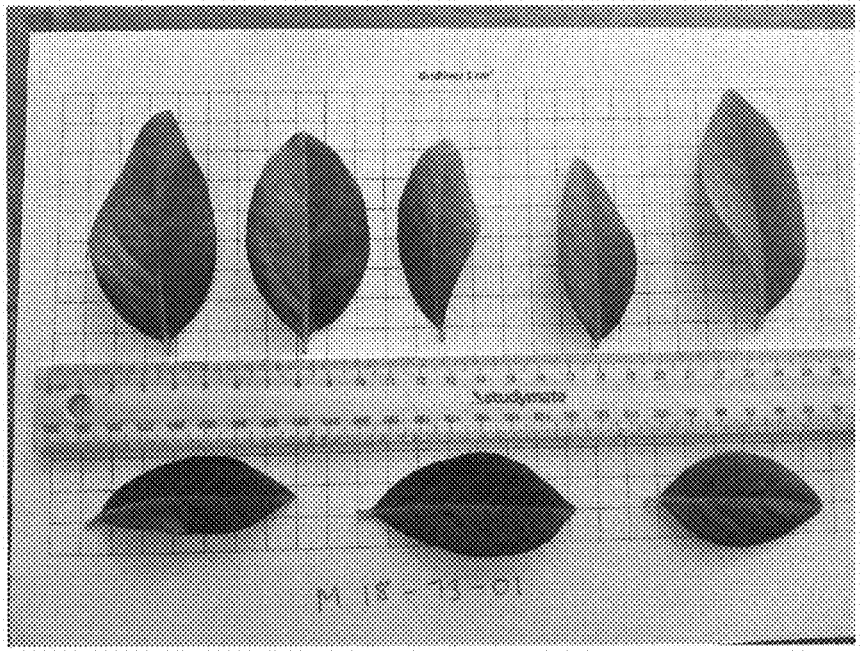
FIG. 3 is a photograph of the upper surface of the leaves of the new variety 'Ridley7301'.
Figure 4:
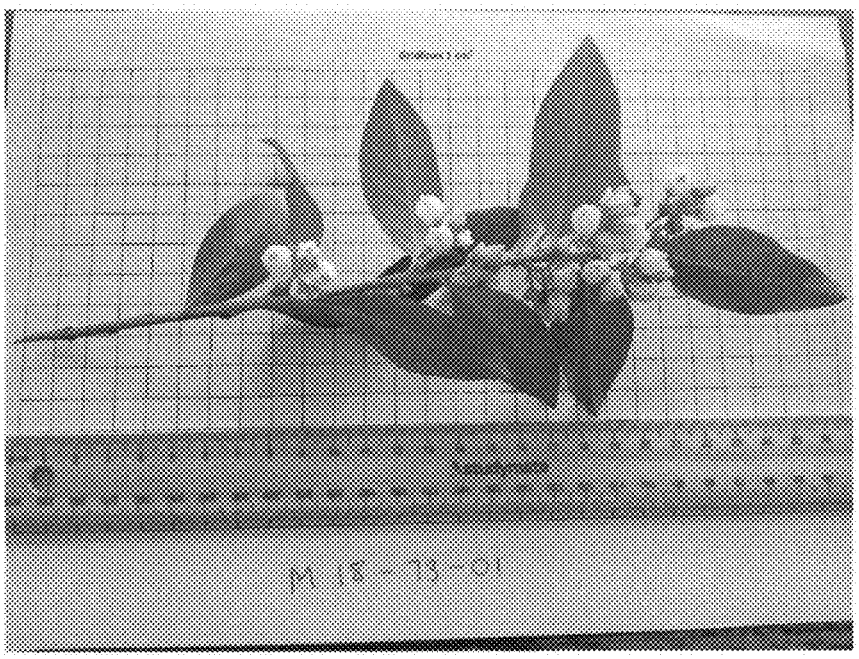
FIG. 4 is a photograph of the flower cluster of the new variety 'Ridley7301'.
Figure 5:
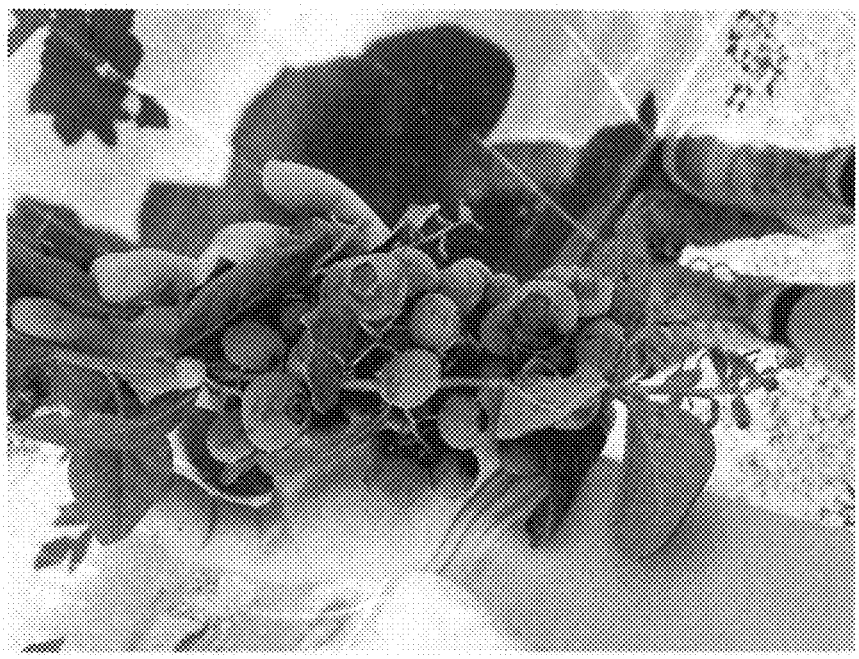
FIG. 5 is a photograph of the fruit cluster of the new variety 'Ridley7301'.

The following detailed description sets forth the distinctive characteristics of 'Ridley7301'. The data which define these characteristics were collected from asexual reproductions of the original selection. Dimensions, sizes, colors, and other characteristics are approximations and averages set forth as accurately as possible. The plant history was taken on plants approximately 3 years of age, and the descriptions relate to plants grown in the field in Tabulam from 2020-2023, New South Wales, Australia. Descriptions of fruit characteristics were made on fruit grown in Tabulam, New South Wales, Australia. Color designations are from Tabulam, New South Wales, Australia. Color notations are based on *The Royal Horticultural Society Colour Chart*, of The Royal Horticultural Society, London, sixth edition.

Classification:
- a. *Family*.—Ericaceae.
- b. *Genus*.—*Vaccinium*.
- c. *Species*.—Hybrid.
- d. *Common name*.—Southern Highbush Blueberry.

Parentage:
- a. *Female parent*.—'M07-05-03' (unpatented).
- b. *Male parent*.—'Ridley 4507' (unpatented).

Market class: A fruiting plant intended for use as fresh fruit for shipping, hand pick, customer pick, machine harvest and processing markets and as a home garden plant.

PLANT

General:
- a. *Plant height*.—Average 1.71 m.
- b. *Plant width*.—Average 1.65 m.
- c. *Growth habit*.—Upright to semi-upright.
- d. *Growth*.—Strong.
- e. *Productivity*.—Approximately 9 kg/year on 3 year old plants.
- f. *Cold hardiness*.—Has not been tested/expected to be low.
- g. *Cold tolerance*.—Has not been tested/expected to be low.
- h. *Chilling requirement*.—Low (under 600 hours).
- i. *Fruiting type*.—On one-year-old and current season shoots. Predominantly on one-year-old shoots with conventional pruning.
- j. *Tolerance to disease*.—Has not been tested.
- k. *Leafing*.—Vegetative bud burst is medium.
- l. *Twigginess*.—Moderate.

STEM

General:
- a. *Suckering tendency*.—Nil-low.
- b. *Mature cane color*.—201D.
- c. *Mature cane length*.—154 cm.
- d. *Mature cane width*.—23 mm.
- e. *Bark texture*.—Moderately rough, typical of species.
- f. *Surface texture of new wood*.—Smooth.
- g. *Internode length on strong, new shoots*.—11-35 mm; 21.8 mm average.
- h. *Fruiting wood*.—Up to 22 cm in length; 18 cm average.

FOLIAGE

General:
- a. *Time of beginning of leaf bud burst*.—Early-Mid (from approximately week 38 onwards at Tabulam, NSW, Australia).
- b. *Leaf color* (*top side*).—NN137A.
- c. *Leaf color* (*under side*).—147D.
- d. *Leaf arrangement*.—Alternate.
- e. *Leaf shape*.—Ovate/Elliptic.
- f. *Leaf margins*.—Overall entire on UPOV TQ scale. Slightly crenate.
- g. *Undulation of margin*.—Weak.
- h. *Leaf venation*.—Reticulate.
- i. *Leaf apices*.—Acute.
- j. *Leaf bases*.—Acute.
- k. *Leaf length* (*without petiole*).—Average 68 mm.
- l. *Leaf width*.—Average 34 mm.
- m. *Leaf length/width ratio*.—2:1.
- n. *Leaf nectaries*.—Absent.
- o. *Leaf glaucosity on upper side*.—Medium.
- p. *Pubescence of upper side*.—Absent.
- q. *Pubescence of lower side*.—Absent.
- r. *Cross sectional profile*.—Flat.
- s. *Longitudinal profile*.—Slightly concave.
- t. *Attitude*.—Semi-upright.

Petioles:
- a. *Length*.—Average 4.9 mm.
- b. *Width*.—Average 2 mm.
- c. *Color*.—144C.

FLOWERS

General:
- a. *Time of beginning of flowering*.—Mid (week 17 at Tabulam, NSW Australia).
- b. *Time of* 50% *anthesis*.—Week 27 at Tabulam, NSW Australia.
- c. *Flower shape*.—Urceolate.
- d. *Flower bud density*.—Moderate.
- e. *Flower fragrance*.—Absent to weak, sweet.

Corolla:
a. *Color.*—155A.
b. *Length.*—9-11 mm.
c. *Width.*—6-8 mm average.
d. *Aperture width.*—3-5 mm.
e. *Anthocyanin coloration of corolla.*—Absent to weak.
f. *Corolla ridges.*—Present.
g. *Protrusion of stigma.*—Nil.

Inflorescence:
a. *Length.*—28-36 mm, average 31 mm.
b. *Diameter.*—Average 32 mm.
c. *Length of peduncle.*—Average 17.7 mm.
d. *Surface texture of peduncle.*—Smooth.
e. *Color of peduncle.*—144D.
f. *Length of pedicel.*—6 mm average.
g. *Surface texture of pedicel.*—Smooth.
h. *Color of pedicel.*—144D.
i. *Number of flower clusters per piece of fruiting wood.*—4-13, average 8.
j. *Number of flowers per cluster.*—5-9, average 7.
k. *Flower cluster density.*—Moderate.

Calyx (with sepals):
a. *Diameter.*—5-6 mm.
b. *Color of receptacle.*—143B.

Stamen:
a. *Length.*—7 mm.
b. *Number per flower.*—10.
c. *Filament color.*—145D.

Pistil:
a. *Length.*—8-9 mm.
b. *Style length.*—7-8 mm.
c. *Ovary color (exterior).*—145B.

Anther:
a. *Length.*—5 mm.
b. *Number.*—10.
c. *Color.*—N167A.

Pollen:
a. *Abundance.*—High.
b. *Color.*—158C.
c. *Self-compatibility.*—86%.

FRUIT

General:
a. *Time of fruit ripening.*—Early (from week 21-24 in Tabulam, NSW, Australia).
b. *Time of 50% maturity.*—Week 31-35 at Tabulam, NSW, Australia.
c. *Fruit development period.*—40-50 days.
d. *Cluster density.*—Moderate, 5-9 berries per cluster.
e. *Unripe fruit color.*—143C.
f. *Ripe berry color (fruit bloom removed).*—203B.
g. *Berry surface wax abundance.*—Strong.
h. *Berry flesh color.*—157C.
i. *Berry weight.*—3 grams.
j. *Berry height from calyx to scar.*—13 mm.
k. *Berry diameter.*—21 mm.
l. *Berry shape.*—Oblate.
m. *Fruit stem scar.*—Small (dry).
n. *Sweetness when ripe.*—Moderate to high, 13.8° Brix.
o. *Firmness when ripe.*—Firm (69% Durofel).
p. *Acidity when ripe.*—Low to moderate.
q. *Storage quality.*—Performs adequately in storage trials for up to 4 weeks.
r. *Suitability for mechanical harvesting.*—Moderate.
s. *Self-fruitfulness.*—86%.
t. *Uses.*—Fresh fruit for shipping, customer pick and processing markets and as a home garden plant.

SEED

General:
a. *Seed abundance in fruit.*—High.
b. *Seed color.*—165B.
c. *Seed dry weight.*—Not measured.
d. *Seed length.*—1 mm.

COMPARISON BETWEEN PARENTAL AND COMMERCIAL CULTIVARS

When 'Ridley7301' is compared to the seed parent 'M-07-05-03' (unpatented) it can be observed that 'M-07-05-03' has comparatively poor flavor, firmness and plant vigor. 'M-07-05-03' has not been maintained so is not available for further comparison.

Table 1, below, provides comparisons between 'Ridley7301', its pollen parent, 'Ridley 4507' (AU PBR Grant Certificate 6076), and the commercial cultivars that it has the most similarity to, 'Ridley 1602' (U.S. Plant Pat. No. 31,605) and 'Ridley 4514' (U.S. Plant Pat. No. 27,163). The commercial cultivars of most similarity were selected based on similar plant vigor, plant growth habit, fruit cluster density, in accordance with useful grouping characteristics identified in the UPOV test guidelines for blueberries (TG/137/5 Rev).

TABLE 1

| Organ | Context | 'Ridley-7301' | 'Ridley 4507' (AU PBR Cert. 6076) | 'Ridley 1602' (U.S. Plant Pat. No. 31,605) | 'Ridley 4514' (U.S. Plant Pat. No. 27,163) |
|---|---|---|---|---|---|
| Plant | Vigor | Strong | Medium to strong | Strong | Strong to very strong |
| Plant | Growth habit | Upright to semi-upright | Semi-upright | Upright to semi-upright | Upright to semi-upright |
| One-year-old shoot | Color | Greenish red | Greenish red | Green | Green |
| One-year-old shoot | Length of internode | Medium | Medium | Medium | Medium |
| Leaf | Length | Long | Medium | Long to very long | Medium to long |
| Leaf | Width | Broad | Medium | Medium to broad | Broad to very broad |
| Leaf | Shape | Ovate/elliptic | Elliptic | Elliptic | Elliptic |
| Leaf | Color of upper side | Green | Green | Green | Green |
| Leaf | Intensity of green color on upper side (varieties with green leaf color only) | Medium | Light to medium | Medium | Medium |
| Leaf | Margin | Entire | Entire | Entire | Entire |
| Flower bud | Anthocyanin coloration | Weak | Weak | Medium | Weak |
| Flower | Shape of corolla | Urceolate | Urceolate | Urceolate | Urceolate |
| Flower | Size of corolla tube | Medium | Medium | Medium | Medium |

TABLE 1-continued

| Organ | Context | 'Ridley-7301' | 'Ridley 4507' (AU PBR Cert. 6076) | 'Ridley 1602' (U.S. Plant Pat. No. 31,605) | 'Ridley 4514' (U.S. Plant Pat. No. 27,163) |
|---|---|---|---|---|---|
| Flower | Anthocyanin coloration of corolla tube | Absent or very weak | Absent or very weak | Absent or very weak | Absent or very weak |
| Flower | Ridges on corolla | Present | Present | Present | Present |
| Fruit cluster | Density | Medium | Medium | Medium | Medium |
| Unripe fruit | Intensity of green color | Light | Light | Light | Light |
| Fruit | Size | Very large | Large | Large | Large |
| Fruit | Shape in longitudinal section | Oblate | Oblate | Oblate | Oblate |
| Fruit | Attitude of sepals | Straight | Straight | Straight | Straight |
| Fruit | Diameter of calyx basin | Large | Medium to large | Large | Medium to large |
| Fruit | Depth of calyx basin | Medium to deep | Deep | Deep | Deep |

TABLE 1-continued

| Organ | Context | 'Ridley-7301' | 'Ridley 4507' (AU PBR Cert. 6076) | 'Ridley 1602' (U.S. Plant Pat. No. 31,605) | 'Ridley 4514' (U.S. Plant Pat. No. 27,163) |
|---|---|---|---|---|---|
| Fruit | Intensity of bloom | Strong | Strong | Strong | Strong |
| Fruit | Color of skin | Dark blue | Dark blue | Dark blue | Dark blue |
| Fruit | Firmness | Firm | Firm | Very firm | Firm |
| Fruit | Sweetness | Medium to high | High to very high | High to very high | Medium to high |
| Fruit | Acidity | Low to medium | Medium | Medium to high | Low |
| Time of | Vegetative bud burst | Medium | Medium to late | Very early | Late |
| Time of | Beginning of flowering | Early | Early to medium | Very early to early | Very early |
| Time of | Beginning of fruit ripening | Early | Early to medium | Very early to early | Early to medium |

The invention claimed is:

1. A new and distinct variety of blueberry plant named 'Ridley7301', as illustrated and described herein.

* * * * *